(12) United States Patent
Booksh et al.

(10) Patent No.: US 9,207,117 B2
(45) Date of Patent: Dec. 8, 2015

(54) APPARATUS AND METHOD FOR PERFORMING SURFACE PLASMON RESONANCE (SPR) SPECTROSCOPY WITH AN INFRARED (IR) SPECTROMETER

(75) Inventors: Karl Booksh, Hockessin, DE (US); Nicola Menegazzo, Newark, DE (US); Yoon-Chang Kim, Newark, DE (US); Derrick Allen, Claymont, DE (US); Lauren Kegel, Newark, DE (US)

(73) Assignee: University of Delaware, Newark, DE (US)

(*) Notice: Subject to any disclaimer, the term of this patent is extended or adjusted under 35 U.S.C. 154(b) by 411 days.

(21) Appl. No.: 13/812,323

(22) PCT Filed: Jul. 28, 2011

(86) PCT No.: PCT/US2011/045716
§ 371 (c)(1),
(2), (4) Date: Jun. 5, 2013

(87) PCT Pub. No.: WO2012/016037
PCT Pub. Date: Feb. 2, 2012

(65) Prior Publication Data
US 2013/0240734 A1 Sep. 19, 2013

Related U.S. Application Data

(60) Provisional application No. 61/368,389, filed on Jul. 28, 2010, provisional application No. 61/421,346, filed on Dec. 9, 2010.

(51) Int. Cl.
*G02B 5/20* (2006.01)
*G01J 3/42* (2006.01)
(Continued)

(52) U.S. Cl.
CPC ............. *G01J 3/0205* (2013.01); *G01J 3/42* (2013.01); *G01N 21/553* (2013.01); *G02B 5/208* (2013.01); *G01N 21/35* (2013.01)

(58) Field of Classification Search
CPC .......... G01J 3/0205; G01J 3/42; G01N 21/35; G01N 21/553; G02B 5/208
See application file for complete search history.

(56) References Cited

U.S. PATENT DOCUMENTS 5,485,277 A 1/1996 Foster
6,330,062 B1 12/2001 Corn et al.
(Continued)

FOREIGN PATENT DOCUMENTS

JP 06-050882 2/1994
JP 2002-257731 9/2002

OTHER PUBLICATIONS

Lucania et al., "Near Critical Angle FTIR ATR Spectroscopy With a Variable Angle Reflection Accessory", Application Note No. 60501, Mar. 15, 2006.
(Continued)

*Primary Examiner* — Mark R Gaworecki
(74) *Attorney, Agent, or Firm* — RatnerPrestia

(57) ABSTRACT

Methods of measuring a sample characteristic and accessories for infrared (IR) spectrometers are provided. An accessory includes an input port and an output port having an optical path therebetween, a surface plasmon resonance (SPR) structure for contacting a sample, a mirror system, and an optical element for producing collimated light. The SPR structure produces internally reflected light responsive to broadband IR light, modified by a SPR between the SPR structure and the sample. The mirror system directs the broadband IR light from the input port to the SPR structure and directs the internally reflected light from the SPR structure to the output port, producing output light indicative of a characteristic of the sample associated with the SPR. The optical element is disposed along the optical path between the input port and the output port.

24 Claims, 14 Drawing Sheets

(51) Int. Cl.
  *G01N 21/35* (2014.01)
  *G01N 21/552* (2014.01)
  *G01J 3/02* (2006.01)

(56) References Cited

U.S. PATENT DOCUMENTS 7,265,844 B2  9/2007  Codner et al.
7,576,863 B2  8/2009  Weibel

OTHER PUBLICATIONS

Lucania et al., "Aperture Design for Near Critical Angle FTIR ATR Spectroscopy", Application Note No. 70318, Feb. 28, 2007.
Zangeneh, et al., "Surface Plasmon Spectral Fingerprinting of Adsorbed Magnesium Phthalocyanine by Angle and Wavelength Modulation", Applied Spectroscopy, vol. 58, No. 1, 2004.
International Search Report for International Application No. PCT/US2011/045716, dated Apr. 9, 2012.
Homola, J., "Surface Plasmon Resonance Sensors for Detection of Chemical and Biological Species," Chem. Rev. 108, (2008) 462-493.
Johnson, P.B and Christy, R.W., "Optical Constants of the Nobel Metals," Physical Review B, 6: 12 (1972) 4370-4379.
Golosovsky, M. et al., "Midinfrared surface-plasmon resonance: A novel biophysical tool for studying living cells," Journal of Applied Physics, 105 (2009) 102036/1-11.
Masson, J.-F., et al., "Fiber-Optic Surface Plasmon Resonance Sensors in the Near-Infrared Spectral Region," Applied Spectroscopy, 60: 11 (2006) 1241-1246.
Nelson, B.P., et al., "Near-Infrared Surface Plasmon Resonance Measurements of Ultrathin Films. 1. Angle Shift and SPR Imaging Experiments," Analytical Chemistry, 71: 18 (1999) 3928-3934.
Frutos, A. G., et al. "Near-Infrared Surface Plasmon Resonance Measurements of Ultrathin Films. 2. Fourier Transform SPR Spectroscopy," Analytical Chemistry, 71: 18 (1999) 3935-3940.
Köβlinger, C., et al., "Comparison of the QCM and the SPR method for surface studies and immunological applications," Sensors and Actuators B, 24-25, (1995) 107-112.
GWC_Technologies, "Fourier-Transform SPR System: The SPR100," Edition edn., (2010).
Live, L.S., et al., "Propagating Surface Plasmon Resonance on Microhole Arrays," Analytical Chemistry, 82: 9 (2010) 3780-3787.
Kano, H., et al., "Surface-plasmon sensor for absorption-sensitivity enhancement," Applied Optics, 33: 22 (1994) 5166-5170.
Ikehata, A., et al., "Surface Plasmon Resonance Near-Infrared Spectroscopy," Analytical Chemistry, 76: 21 (2004) 6461-6469.
Ikehata, A., et al., "Quantitative Analyses of Absorption-Sensitive Surface Plasmon Resonance Near-Infrared Spectra," Applied Spectroscopy, 60: 7 (2006) 747-751.
Segelstein, D.J., "The Complex Refractive Index of Water," A Thesis in Physics, University of Missouri (1981).
Johansen, K., et al., "Imaging surface plasmon resonance sensor based on multiple wavelengths: Sensitivity considerations," Review of Scientific Instruments, 71:9 (2000) 3530-3538.
Peterson, A.W., et al., "Surface plasmon resonance imaging of cells and surface-associated fibronectin," BMC Cell Biology, 10:16 (2009), 17 pages.
Singh, B.K., et al., "Multicolor Surface Plasmon Resonance Imaging of Ink Jet-Printed Protein Microarrays," Analytical Chemistry, 79: 14 (2007) 5124-5132.
Curcio, J.A., et al., "The Near Infrared Absorption Spectrum of Liquid Water," Journal of the Optical Society of America, 41: 5 (1951) 302-304.
Reichert Technologies Products, "$r^2$ i300 Refractometer User Guide," Edition edn., 2003.
Krüss_Optronic, "Refractometers," Edition edn., 2013.
Schmidt_+_Haensch, "ATR W Series," Edition edn., 2014.
Bolduc, O.R., et al., "High-resolution surface plasmon resonance sensors based on a dove prism," Talanta, 77 (2009) 1680-1687.
Jorgenson, R.C., et al., "A fiber-optic chemical sensor based on surface plasmon resonance," Sensors and Actuators B, 12 (1993) 213-220.
Jung, L., et al., "Quantitative Interpretation of the Response of Surface Plasmon Resonance Sensors to Adsorbed Films," Langmuir, 14 (1998) 5636-5648.
Li, Ying-Chang et al., "Differential-Phase Surface Plasmon Resonance Biosensor," Analytical Chemistry, 80: 14 (2008) 5590-5595.
Pollet, J., et al., "Fiber optic SPR biosensing of DNA hybridization and DNA-protein interactions," Biosensors and Bioelectronics 25 (2009) 864-869.
Written Opinion for International Application No. PCT/US2011/045716, mailed Feb. 7, 2013.

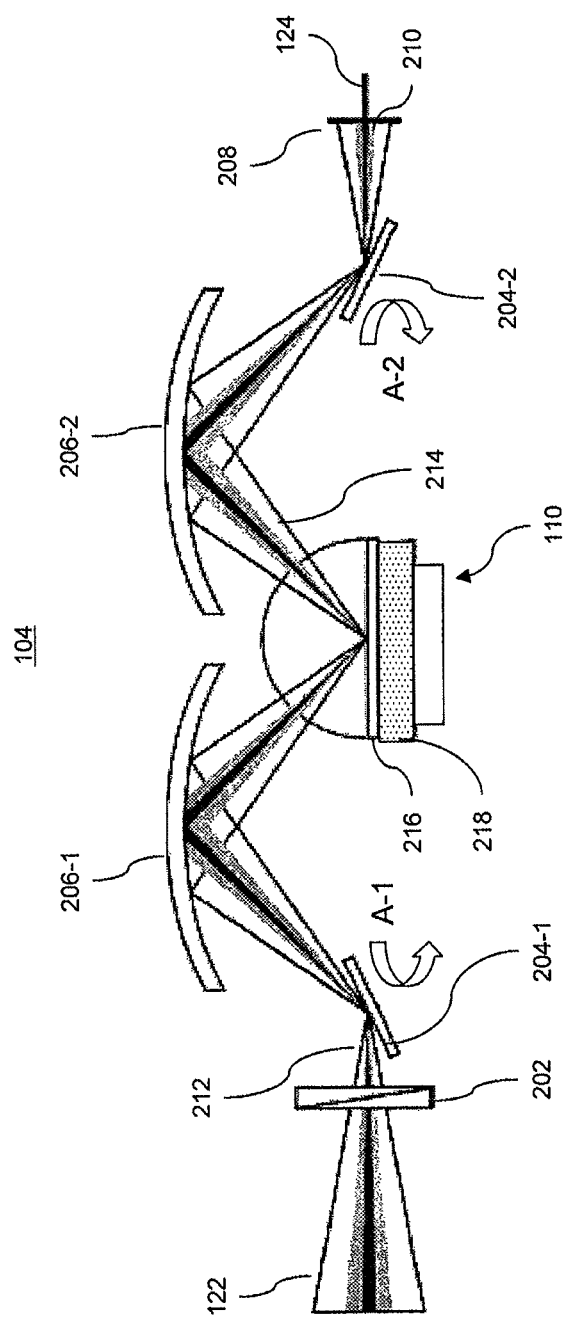
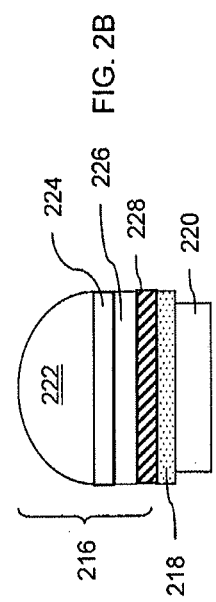
FIG. 2A
FIG. 2B

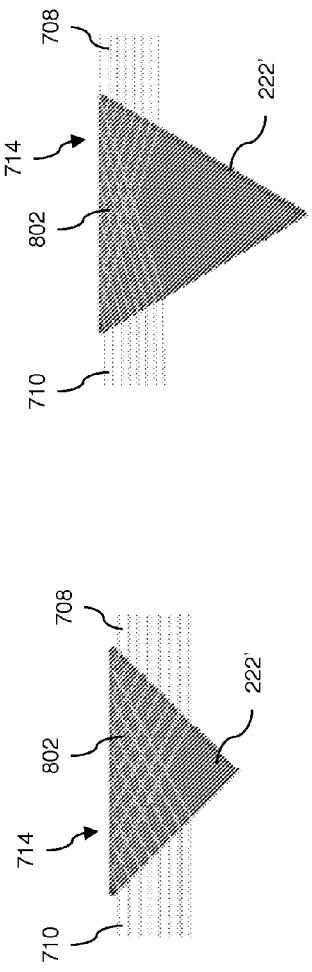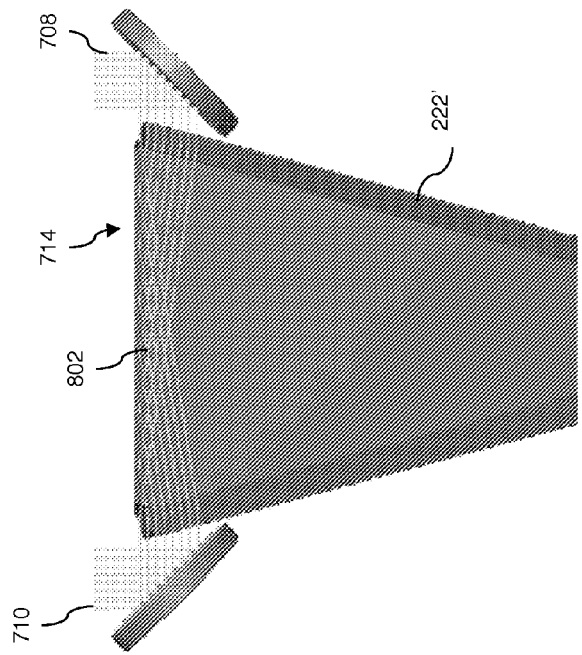

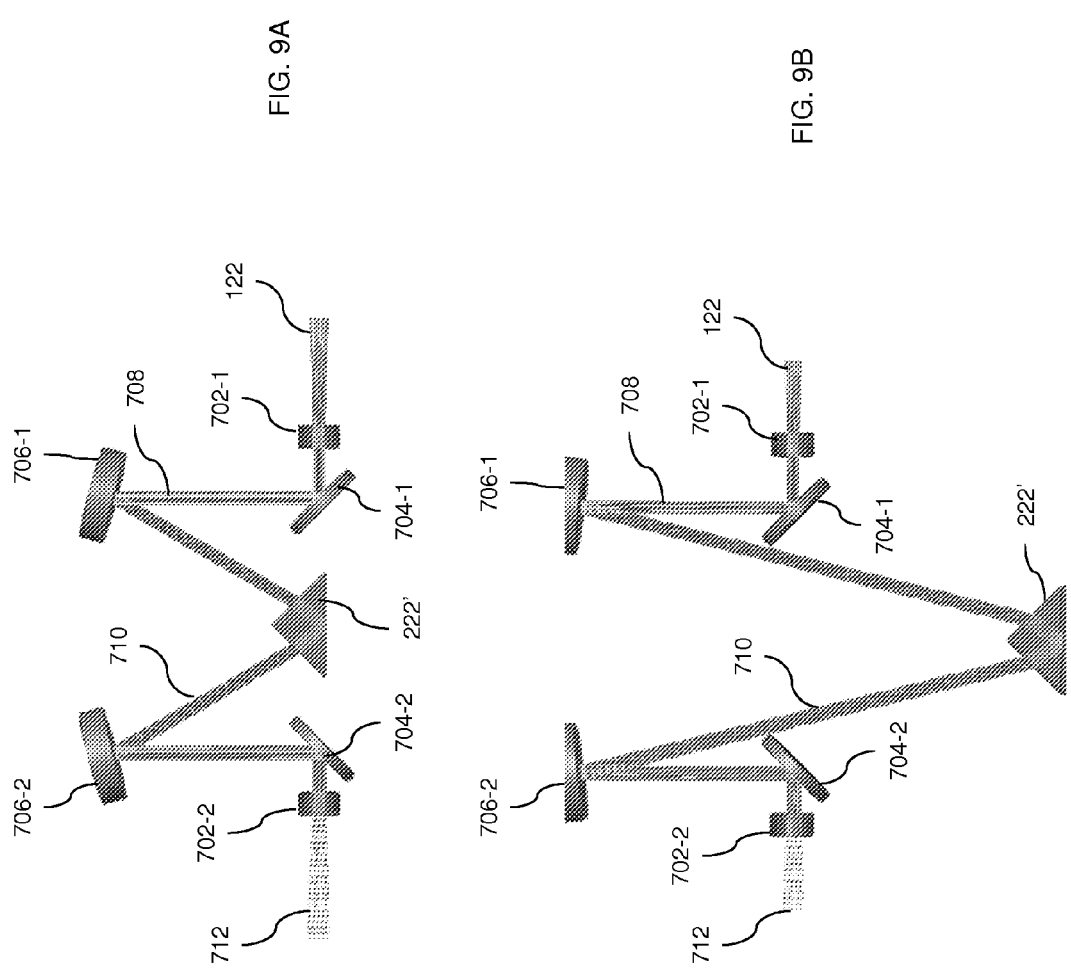

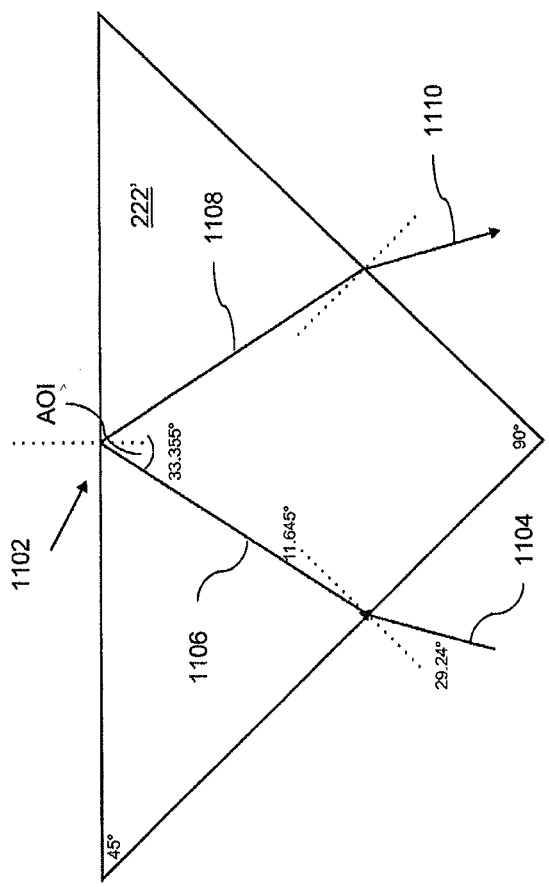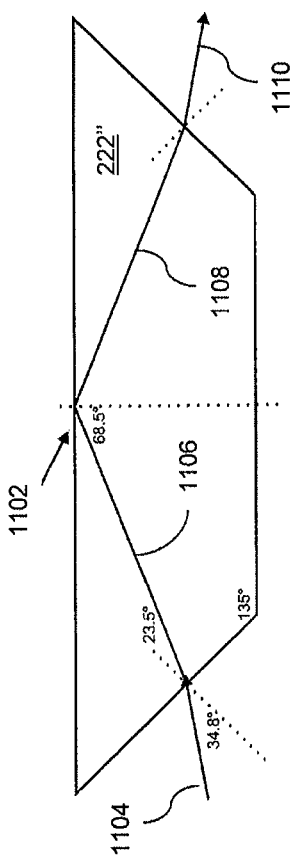

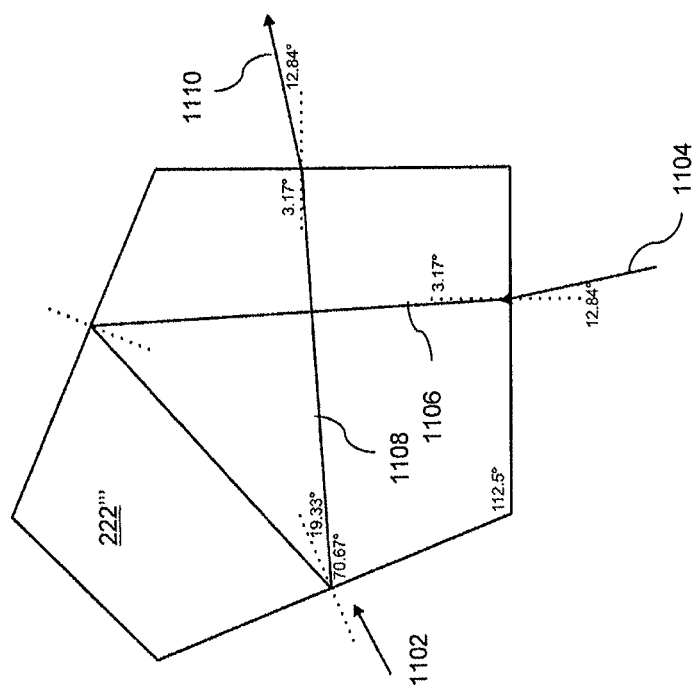

APPARATUS AND METHOD FOR PERFORMING SURFACE PLASMON RESONANCE (SPR) SPECTROSCOPY WITH AN INFRARED (IR) SPECTROMETER

CROSS REFERENCE TO RELATED APPLICATIONS

This application is a National Phase of International Application No. PCT/US2011/045716, filed Jul. 28, 2011, entitled APPARATUS AND METHOD FOR PERFORMING SURFACE PLASMON RESONANCE (SPR) SPECTROSCOPY WITH AN INFRARED (IR) SPECTROMETER which claims priority to U.S. Provisional Application Ser. No. 61/368,389, entitled "APPARATUS AND METHOD FOR PERFORMING SURFACE PLASMON RESONANCE (SPR) SPECTROSCOPY WITH A FOURIER TRANSFORM INFRARED (FT-IR) ACCESSORY," filed Jul. 28, 2010, incorporated fully herein by reference. Additionally, this application claims priority to U.S. Provisional Application Ser. No. 61/421,346, entitled "APPARATUS AND METHOD FOR PERFORMING SURFACE PLASMON RESONANCE (SPR) SPECTROSCOPY WITH A FOURIER TRANSFORM INFRARED (FT-IR) ACCESSORY," filed Dec. 9, 2010, incorporated fully herein by reference.

STATEMENT REGARDING FEDERALLY SPONSORED RESEARCH

The present invention was supported in part by Grant Number 5R01EB004761 from the National Institutes of Health. The United States Government may have certain rights to the invention.

FIELD OF THE INVENTION

The present invention relates to surface plasmon resonance (SPR) spectroscopy and, more particularly, to methods and infrared (IR) spectroscopy accessories for performing surface plasmon resonance (SPR) spectroscopy.

BACKGROUND OF THE INVENTION

Surface plasmons, also known as surface plasmon polaritons, are electromagnetic waves that propagate at an interface between a metal and a dielectric, in a direction parallel to the boundary between the metal and dielectric. Because the electromagnetic wave propagates on the boundary of the metal and the dielectric, oscillations of the electromagnetic wave may change with irregularities on the boundary, such as, for example, due to the adsorption of molecules to the metal surface. When the surface plasmon encounters a molecule on the metal/dielectric boundary, the molecule may absorb energy from the plasmon and re-emit it as light which is reflected from the metal film.

Surface plasmons may be used to detect molecular adsorption of samples, such as polymers, proteins, etc., by measuring changes in the angle of light reflected from the metal/dielectric boundary. Typically, resonant excitation of surface plasmons (i.e., SPR) is used, where, under resonant conditions, the metal will absorb light energy at a certain angle of incidence (AOI). At this particular AOI, the intensity of the reflected light is decreased, typically evidenced as a sharp dip in the intensity. The AOI at which resonance occurs is affected by the refractive index of the sample layer disposed on the metal. Accordingly, the AOI corresponding to resonance may be used as a direct measure of the characteristics of the sample.

SUMMARY OF THE INVENTION

The present invention is embodied in an accessory for an infrared (IR) spectrometer. The accessory includes an input port and an output port having an optical path therebetween. The accessory also includes a surface plasmon resonance (SPR) structure for contacting a sample and a mirror system. The SPR structure is configured to produce internally reflected light responsive to broadband IR light. The internally reflected light is modified by a surface plasmon-polariton resonance produced between the SPR structure and the sample. The mirror system is configured to direct the broadband IR light from the input port to the SPR structure and to direct the internally reflected light from the SPR structure to the output port, to produce output light indicative of a characteristic of the sample associated with the surface plasmon resonance. The accessory further includes an optical element disposed along the optical path between the input port and the output port, configured to produce collimated light.

The present invention is also embodied in a method of measuring a characteristic of a sample. The method includes the steps of: directing broadband infrared (IR) light via a mirror system to a surface plasmon resonance (SPR) structure for contacting the sample; internally reflecting the broadband IR light at an interface between the SPR structure and the sample, producing at the interface a surface plasmon resonance that modifies the internally reflected light; directing the internally reflected light from the SPR structure via the mirror system to produce output light indicative of the surface plasmon resonance; and measuring the output light to determine the characteristic of the sample. The characteristic is associated with the surface plasmon resonance. The broadband IR light or the output light is collimated.

BRIEF DESCRIPTION OF THE DRAWINGS

The invention may be understood from the following detailed description when read in connection with the accompanying drawings. It is emphasized that, according to common practice, various features of the drawings may not be drawn to scale. On the contrary, the dimensions of the various features may be expanded or reduced for clarity. Moreover, in the drawings, common numerical references are used to represent like features. Included in the drawings are the following figures:

FIG. 2A is a schematic diagram of an exemplary SPR accessory used in the spectrometer shown in FIG. 1, according to an embodiment of the present invention;

FIG. 2B is a cross-sectional diagram of an exemplary sample cell of the SPR accessory shown in FIG. 2A, according to an embodiment of the present invention;

FIGS. 8A, 8B and 8C are cross-sectional diagrams of exemplary prisms of the sample cell shown in FIG. 7B, illustrating a relationship between prism shape and the angle of light directed to the active surface of prism, according to embodiments of the present invention;

FIGS. 9A and 9B are schematic diagrams of an exemplary SPR accessory illustrating control of the light beam directed to a sample cell via positioning of the sample cell and the mirror system, according to an embodiment of the present invention;

FIGS. 11A, 11B and 11C are cross-section diagrams of exemplary prisms of a sample cell, according to embodiments of the present invention.

DETAILED DESCRIPTION OF THE INVENTION

In a conventional IR spectrometer (such as a Fourier Transform infrared (FT-IR) spectrometer), a broadband optical beam is focused on a sample in a transmission optical design, such that the optical beam transmitted through the sample is measured to obtain an infrared spectrum of absorption by the sample. A conventional IR accessory may be integrated into the sample compartment of the IR spectrometer, to steer and refocus the beam on the sample at a user controlled angle in a reflectance optical design (to measure the optical beam that is reflected by the sample).

Aspects of the invention relate to a variable angle IR reflectance spectroscopy accessory (also referred to herein as an SPR accessory) configured to enable SPR spectroscopy by an IR spectrometer. Exemplary SPR accessories may also be configured to enable SPR imaging with a focal plane array (FPA) detector. Exemplary SPR accessories may collimate a focused optical beam in a sample compartment of the IR spectrometer, redirect the collimated beam in a reflectance optical design and may refocus the beam (as modified by the sample) into the original optical path. By using collimated light, variable wavelength SPR spectroscopy may be achieved.

Figure 1:
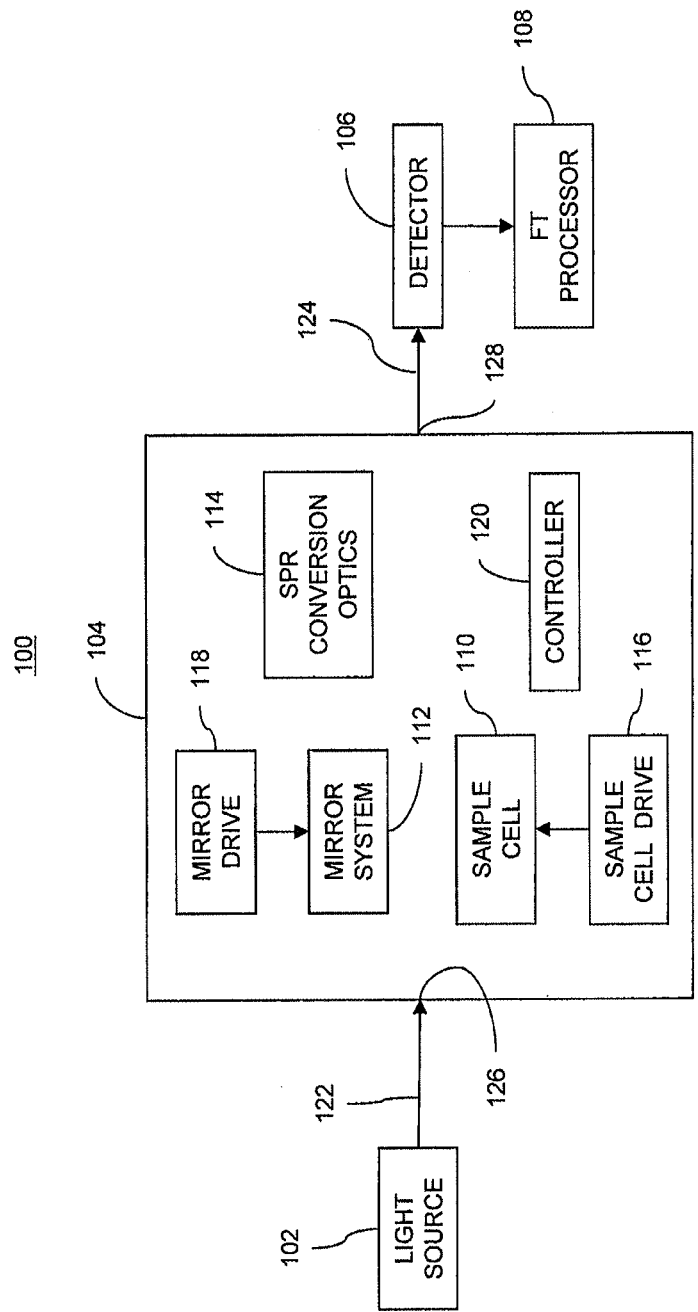
FIG. 1 is a functional block diagram of an exemplary IR spectrometer for SPR spectrometry, according to an embodiment of the present invention.

Referring to FIG. 1, a functional block diagram of exemplary IR spectrometer 100 (referred to herein as spectrometer 100) is shown. According to one embodiment, spectrometer 100 includes light source 102, SPR accessory 104 and detector 106. For example, spectrometer 100 may include a dispersive spectrometer or a Hadamard transform spectrometer.

According to another embodiment, spectrometer 100 may also include Fourier Transform (FT) processor 108, such that spectrometer 100 may represent a FT-IR spectrometer.

Light source 102 is configured to produce light beam 122 of broadband infrared (IR) light. SPR accessory 104 is configured to be positioned in the optical path of light beam 122, to receive light beam 122. SPR accessory 104 may be positioned, for example, in a sample compartment of spectrometer 100.

SPR accessory 104 may include sample cell 110, mirror system 112 and SPR conversion optics 114. Translation of sample cell 110 may be controlled by sample cell drive 116. A rotational position of one or more mirrors of mirror system 112 may controlled by mirror drive 118. Sample cell drive 116 and mirror drive 118 may include, for example, a screw gauge or a stepper motor. SPR accessory 104 may include controller 120 configured to control sample cell drive 116 and mirror drive 118. Controller 120 may be any type of controller (for example, a microprocessor or a field programmable gate array (FPGA)) having a processor execution capability provided by a software program stored in a non-transitory computer readable medium, or a hardwired program provided by an integrated circuit. One or more mirrors of mirror system 112 (and/or a position of sample cell 116) may be rotatably adjusted to change the angle of incidence of light beam 122 on sample cell 110, in order to measure an SPR reflection minimum of a sample on sample cell 110.

An exemplary sample cell 110 is described further below with respect to FIGS. 2B and 7B. In general, sample cell 110 is configured to produce internally reflected light, responsive to broadband light beam 122, which is modified by SPR produced between an SPR structure and a sample.

An exemplary mirror system 112 is described further below with respect to FIGS. 2A and 7A. In general, mirror system 112 includes a plurality of mirrors and is configured to direct light beam 122 from input port 126 to sample cell 110. Mirror system 112 is also configured to direct internally reflected light from sample cell 110 to output port 128.

Exemplary SPR conversion optics 114 are described further below with respect to FIGS. 2A and 7A. In general, SPR conversion optics 114 may include optical elements for producing collimated and polarized light. Because SPR conversion optics 114 may produce collimated and polarized light, the light delivered to sample cell 110 may enable SPR spectrometry.

SPR accessory 104 produces output light beam 124, modified by the SPR at sample cell 110, and which is output via output port 128. Light beam 124 may be provided to detector 106, for SPR spectrometry. Detector 106 may include any suitable detector having a high sensitivity in an appropriate spectral region. Detector 106 may include, without being limited to, silicon (Si) detectors, germanium (Ge) detectors, indium arsenide (InAs) detectors, indium gallium arsenide (InGaAs) detectors and mercury-cadmium-telluride (MCT) detectors. Detector 106 may also include focal plane array (FPA) detectors. An output signal from detector 106 may be output directly from detector 106. An output signal from detector may be processed using conventional Fourier Transform techniques by FT processor 108, to produce an SPR spectrogram of a sample on sample cell 110.

According to embodiments of the invention, SPR measurements may be made by SPR accessory 104 in IR spectrometer 100 using existing light source 102 and detector 106. Conventional variable angle accessories, such as the Auto Seagull variable angle reflectance accessory manufactured by Harrick Scientific (Pleasantville, N.Y.), are typically designed for straightforward integration into the sample compartment of many conventional IR spectrometers. However these conventional IR accessories use focused light, whereas white-light (i.e., broadband light) SPR techniques use collimated light at the sample. Therefore, SPR accessory 104 (a reflectance accessory), may be integrated directly in an optical path of IR spectrometer 100, and may deliver collimated light to the sample, enabling SPR spectroscopy and imaging SPR analysis. Advantages of this embodiment of the invention may include eliminating external coupling and added optical components (i.e., detectors and mirrors), while achieving higher sensitivities, such as those associated with the plasmonic properties of gold in the near-infrared (NIR) and mid-infrared (MIR) regions.

One conventional SPR accessory for performing SPR with a conventional FT-IR spectrometer is described in U.S. Pat. No. 6,330,062 to Corn et al. However, this conventional accessory is external to the FT-IR accessory and requires its own dedicated detector separate from the detector in the FT-IR spectrometer. By contrast, exemplary SPR accessory 104 may fit seamlessly into an sample compartment of IR spectrometer 100, and may employ an existing IR detector (such as detector 106) for spectral collection.

Referring next to FIGS. 2A and 2B, an exemplary SPR accessory 104 is described. In particular, FIG. 2A is a schematic diagram of SPR accessory 104; and FIG. 2B is a cross-sectional diagram of sample cell 110.

Referring to FIG. 2A, SPR accessory 104 includes polarizer 202, planar tiltable mirrors 204-1, 204-2, fixed elliptical mirrors 206-1, 206-1, sample cell 110 and plane 208 having aperture 210. Tiltable mirrors 204-1, 204-2 and fixed elliptical mirrors 206-1, 206-1 represent mirror system 112 (FIG. 1). Tiltable mirrors 204-1, 204-2 are configured to be rotatably positioned, as indicated by respective arrows A-1, A-2, for example by mirror drive 118 (FIG. 1). Polarizer 202 and plane 208 having aperture 210 represent SPR conversion optics 114 (FIG. 1).

In operation, polarizer 202 is configured to receive (unpolarized) broadband light beam 122 and to convert broadband light beam 122 into polarized light beam 212 (referred to herein as polarized beam 212). Polarized beam 212 is directed by tiltable mirror 204-1 to fixed elliptical mirror 206-1. Elliptical mirror 206-1 focuses polarized beam 212 onto sample cell 110. Polarized beam 212 may be coupled into the surface plasmon mode in sample cell 110, because its electric field vector oscillates normal to the plane containing plasmonic material film 228 (described further below with respect to FIG. 2B). Tiltable mirrors 204-1, 204-2 may be simultaneously adjusted to direct polarized beam 212 to sample cell 110 at different incident angles.

In an exemplary embodiment, polarizer 202 includes a visible-near-infrared linear polarizer, model number LPNIR050 manufactured by Thorlabs (Newton, N.J.). Polarizer 202 may include any suitable polarizer capable of providing polarized light beam 212 in an appropriate spectral region. Suitable planar tiltable mirrors 204, elliptical mirrors 206 and polarizer 202 may be understood by the skilled person from the description herein.

Referring to FIGS. 2A and 2B, exemplary sample cell 110 is further described. Sample cell 110 includes SPR structure 216 and sample 218 to be analyzed. SPR structure may include prism 222 and film 228 of plasmonic material. A first surface of film 228 may be disposed on coverslip 226. A refractive index (RI) matching fluid 224 may be disposed between prism 222 and coverslip 226, to provide intimate optical contact between prism 222 and coverslip 226. For example, matching fluid 224 may be selected to have an RI of about 1.5120 for coverslip 226 coated with film 228 of gold.

Sample 218 may be deposited on a second surface of film 228 opposite to the first surface. Fluid flow cell 220 may be configured to be in contact with film 228, for delivering sample 218 for deposit on film 228. Although not shown, a holder may be used to mount sample cell 110. Sample cell 110 may also be coupled to sample cell drive 116 (FIG. 1), which may translate sample cell 110 relative to elliptical mirrors 206-1, 206-2 (for example, as shown in FIGS. 9A and 9B).

Polarized beam 212 (as focused by elliptical mirror 206-1) is directed through prism 222 and onto film 228. Polarized beam 212 undergoes internal reflection in prism 222 and is reflected off of film 228 and out of sample cell 110. In an exemplary embodiment, prism 222 is a hemispherical prism formed of BK-7, manufactured by CrystalTechno Ltd. (Moscow, Russia). Although prism 222 is illustrated as a hemispherical prism, it is understood that prism 222 may be formed of any suitable geometry capable of providing total internal reflection of polarized beam 212. For example, prism 222 may include hemispherical prisms, triangular prisms or other polygonal shaped prisms. (For example, see FIGS. 11A-11C, described further below.) As described further below, light beam 214 (referred to herein as SPR modified beam 214) output from prism 222 is modified by SPR produced between SPR structure 216 and sample 218.

Polarized beam 212 is totally internally reflected by prism 222, in order to excite surface plasmons in a resonant manner. The Kretschmann configuration may be used to excite surface plasmons, where the sensing portion of prism 222 may be coated with thin (typically 50 nm) film 228 of plasmonic material (for example, gold). When light is coupled into prism 222 under conditions suitable for total internal reflection, the transverse magnetic (TM) component of the incident light (for example, polarized beam 212) can undergo an energy transfer at the internal reflection point and excite a standing charge in film 228. This process occurs when the wave vector ($k_x$) for incident photons:

$$k_x = k_0 n_D \sin \theta_{inc} \quad (1)$$

matches the wave vector of the standing charge in film 228 as $$k_{SP} = k_0 \sqrt{\frac{\varepsilon_m \varepsilon_s}{\varepsilon_m + \varepsilon_s}} \quad (2)$$

where $\varepsilon_m$ and $\varepsilon_s$ represent the respective dielectric constants of film 228 and sample 218, $n_D$ is the refractive index of prism 222, $\theta_{inc}$ represents the angle of incident light and $k_0$ represents $\omega/c$, or the angular frequency divided by the speed of light in vacuum. The variable $k_0$ is the wavevector of light propagating in vacuum.

If the above condition is met, then the incident photons are coupled into surface plasmon polaritons, electromagnetic waves that propagate at the interface between film 228 and prism 222 and sample 218. The resulting signal is presented as a loss in intensity of certain wavelengths of light reflected back from film 228. In an SPR spectrum, the region with the lowest intensity is commonly referred to as the "SPR dip." The angle or wavelength location of the SPR dip is a function of the dielectric constant of the sample and will shift in accordance to changes in the sample.

Because surface plasmons arise when $k_x = k_{SP}$, the wavelength sensitivity in SPR spectroscopy to dielectric constants is not immediately obvious unless the wavelength dependency of the dielectric constant ($\varepsilon_m$) of the plasmon support film 228 (such as gold) is considered. In this situation, performing SPR analyses in the near-infrared (NIR) and mid-infrared (mid-IR) ranges where the ratio $\Delta \in_m/\Delta\lambda$ (such as the ratio $\Delta \in_{gold}/\Delta\lambda$) is large (where $\lambda$ represents wavelength), may significantly increase the sensitivity to changes in bulk refractive index (RI). Accordingly, the wavelength dependency of the dielectric constant of film 228 (for example, gold) is largely responsible for the sensitivity attributed to changes in the refractive index of sample 218 monitored by SPR spectroscopy. Furthermore, the optical properties of film 228 may be selected such that, when near-infrared (NIR) and/or mid-infrared (mid-IR) wavelengths are used to excite surface plasmons, higher sensitivities to RI changes may be experienced compared to surface plasmons excited with visible wavelengths.

According to an exemplary embodiment, coverslip 226 coated with film 228 of gold is formed on fluid flow cell 220. Although coverslip 226 coated with gold film 228 is described, it is understood that the coverslip 226 may be coated with any suitable plasmonic material, such as, but not limited to, gold, silver, aluminum, metallic nanoparticles, indium tin oxide (ITO), as well as other conducting metal oxides or materials and composites that support a plasmon-polariton.

According to one embodiment, coverslip 226 and prism 222 may be formed separately of a same material, with a suitable RI matching fluid 224 provided therebetween. According to another embodiment, prism 222 and coverslip 226 may be formed, as one fabrication step, by disposing film 228 of a plasmonic material directly on prism 222. For example, gold film 228 may be sputtered onto prism 222. It is contemplated that, in this example, prism 222 may be a hard prism which can be repolished without damage.

TABLE 1

Example Prism Materials

| Material | Range (μm) | Refractive index (n) | General Comments |
|---|---|---|---|
| Germanium (Ge) | 2-11 | 4.0 | Easily re-polished Insoluble in water |
| Zinc sulfide (ZnS) | 0.7-10 | 2.3 | Insoluble in water Harder than zinc selenide, could be an alternative to germanium |
| Silicon (Si) | 1-7 | 3.4 | Insoluble in water Easily re-polished Limited mid-infrared transparency |
| KRS-5 (a type of thallium halogenide) | 0.7-30 | 2.5 | Insoluble in water Toxic, not easily re-polished |
| Calcium fluoride (CaF$_2$) | 0.4-7 | 1.4 | Slightly soluble in water |
| Barium fluoride (BaF$_2$) | 0.4-9.5 | 1.5 | Slightly soluble in water |
| Potassium bromide (KBr) | 0.5-20 | 1.5 | Very soluble in water |
| Sodium chloride (NaCl) | 0.4-12 | 1.5 | Very soluble in water |
| Sapphire (Al$_2$O$_3$) | 0.3-3.4 | 1.8 | Insoluble in water limited mid-infrared transparency |
| IR grade silica (SiO$_2$) | 0.2-3.6 | 1.5 | Insoluble in water limited mid-infrared transparency |

Embodiments of the invention may use typical SPR materials (for example, glass or sapphire) for coverslip 226 and prism 222 or may use "non-traditional" SPR materials. Table 1, above, provides examples of materials which may be suitable for prism 222 and coverslip 226. For example, glass slides (for coverslip 226) (with RI<1.6) may be employed up to about 1.4 μm and sapphire (1.8 RI) is typically limited to about 4 μm. In addition, index matching fluid 224 is typically available for materials of less than 2.1 RI. Accordingly, materials with a refractive index greater than glass are not typically employed with a separate prism 222 and coverslip 226 (where coverslip 226 is coated with film 228 of plasmonic material). To access SPR spectroscopy in a range greater than 1.5 μm, film 228 may be applied directly to prism 222. It is also noted that sapphire is transparent up to 4 μm. Above 4 μm, ZnSe, CaF$_2$, or Ge may be used.

It is understood that prism 222 may be formed from any suitable material for a desired wavelength range, including, for example, glass, sapphire and BK-7). For aqueous samples, suitable materials for prism 222 may include, without being limited to, non-hygroscopic dielectrics, including, but not limited to, CaF$_2$, Ge, zinc selenide (ZnSe), magnesium fluoride (MgF$_2$), BaF$_2$ and Si. Ge, ZnSe and Si are example materials having a RI above that of commercially available matching fluids. Consequently, any plasmonic structure may be applied directly onto prism 222 of the example non-hygroscopic materials.

In all, by judicious choice of materials for SPR structure 216, SPR spectra may be collected from about 0.5 microns to about 20 microns. Glass and sapphire may be employed in the shorter wavelength range (i.e., less than about 4 μm), ZnSe and CaF$_2$ in the mid-range of wavelengths (for example, CaF$_2$ may provide access to wavelengths up to about 8 to 9 μm and ZnSe may provide access to wavelengths up to about 14.5 μm), and Ge to access wavelengths as high as about 16 μm.

Referring back to FIG. 2A, SPR modified beam 214 output from prism 222 is directed to fixed elliptical mirror 206-2. Elliptical mirror 206-2 focuses SPR modified beam 214 onto tiltable mirror 204-2 and through aperture 210 of plane 208. SPR modified beam 214 passes through aperture 210 to produce output light beam 124 that is collimated. Accordingly, output light beam 124 is collimated light.

Aperture 210 may include any suitable size for restricting the angular spread of output light beam 124 while providing a suitable signal-to-noise ratio (SNR) of output light beam 124 (described further below with respect to FIG. 4). In an exemplary embodiment, aperture 210 includes a slit having a width between about 0.1 mm to about 4 mm, with the width of the slits being wider or narrower to optimize between spectral resolution and optical throughput.

Although FIG. 2A illustrates polarizer 202 on a distal end of SPR accessory 104, and aperture 210 on a proximal end of SPR accessory 104, aperture 210 may be positioned on the distal end and polarizer 202 may be formed on the proximal end of SPR accessory 104. According to additional embodiments, aperture 210 and polarizer 202 may each be formed on either the distal end or proximal end of SPR accessory 104.

Although FIG. 2A illustrates polarizer 202 for producing polarized beam 212, according to another embodiment, a similar result may be achieved by collecting a reference SPR spectrum of sample 218 in air (refractive index of about 1.0) and a further SPR spectrum of sample 218 in water (refractive index of about 1.33) and comparing the two SPR spectrum.

Referring next to FIGS. 3-6B, spectrometer 100 (FIG. 1) with SPR accessory 104 as shown in FIG. 2A was used to record spectra result from averaging 100 scans for both s- and p-polarized light at a resolution of 4 cm$^{-1}$. Conventional reflectance spectra were collected with parameters identical to SPR spectra, but without a gold-coated coverslip.

Glass coverslips (Fisher Scientific, Fair Lawn, N.J., Ø of 25 mm) for SPR analysis were cleaned by immersion in boiling piranha solution [3:1 (v/v) concentrated H$_2$SO$_4$:30% H$_2$O$_2$] (Fisher Scientific, Fair Lawn, N.J.) for at least 90 minutes, followed by thorough rinsing with deionized water and drying with nitrogen gas (Keen Compressed Gas Co., Wilmington, Del.). The clean coverslips were then immediately placed in a DC magnetron sputtering system (Cressington Scientific Instruments Ltd., model 308R, Watford, UK) and a 5-nm chromium (99.95+%, Kurt J. Lesker Co., Clairton, Pa.) adhesion layer followed by 50 nm of gold (99.99%, ESPI Metals, Ashland, Oreg.) were deposited. The gold-coated coverslips were used immediately following deposition.

In this example, a Bruker Optics (Billerica, Mass.) Vertex 70 FT-IR spectrometer equipped with a halogen bulb broadband NIR light source, room-temperature InGaAs detector, and a calcium fluoride beam splitter was used. In this example, polarizer 202 (FIG. 2A) includes a Thorlabs (Newton, N.J.) LPNIR050 visible-near-infrared linear polarizer on the distal end of the AutoSeagull; slit apertures 210 are 0.2 mm, 1 mm, and 3 mm; prism 222 is a BK-7 ATR hemispherical prism (CrystalTechno Ltd., Moscow, Russia); and RI matching fluid 224 (RI of 1.5120) from Cargille Laboratories (Cedar Grove, N.J.) are used.

The sensitivity of SPR accessory 104 was determined by measuring the SPR dip location with aqueous sucrose (≥99.5°/O, Sigma-Aldrich, St. Louis, Mo.) solutions at concentrations ranging from 1% to 15% (w/w) at room temperature (20° C.). Measurements were initiated by approaching the incident angles from (at least) 20° below the desired value. A measurement series consisted of loading the flow cell 220 (FIG. 2B) with the solution to be tested, collecting s- and p-polarized spectra for each angle, then exchanging the solution with the next higher sucrose concentration. This procedure was repeated in triplicate; therefore, the error bars presented in FIG. 6A below represent the variability in RI measurement coupled with the error associated with changing the incident angle in the system. The theoretical SPR response from a four-layer model system (prism, chromium, gold, sample) was calculated based on Fresnel's equations.

Figure 3:
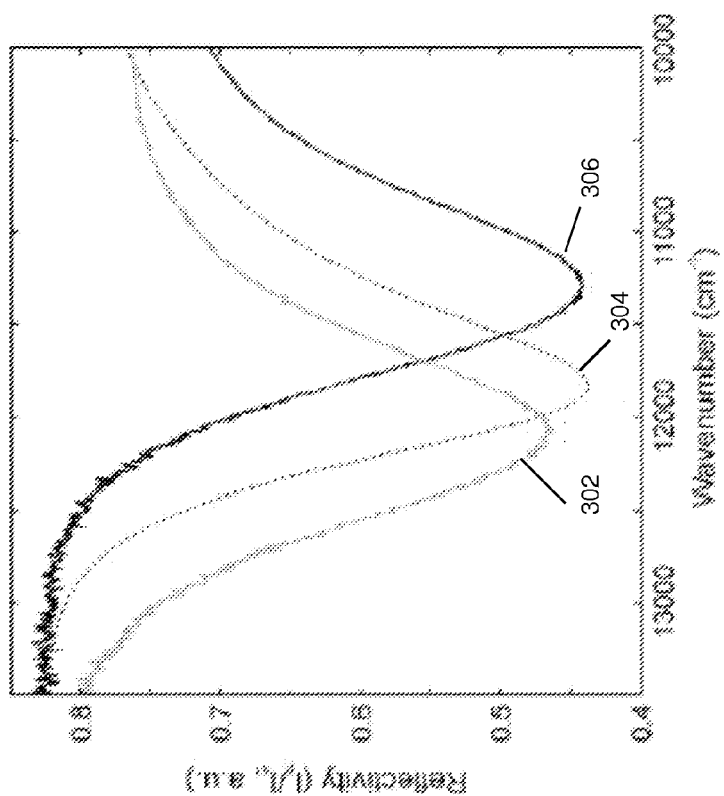
FIG. 3 is a graph of reflectivity as a function of wavenumber illustrating example SPR spectra for various approaching angles, according to an embodiment of the present invention.

Choosing the direction from which the incident angle is approached is important for measurement reproducibility. Referring to FIG. 3, a graph of reflectivity as a function of wavenumber illustrating example SPR spectra for various approaching angles is shown. Spectra 302 and 306 are collected at a nominal incident angle of 65°. The theoretical spectrum 304 from the Fresnel equations is included for comparison. Spectrum 302 resulted following movement of the stepper motors from 85° to 65°, that is, from a higher to a lower angle, whereas spectrum 306 corresponds to the opposite approach direction: from 45° to 65°. Changing the approach direction yields SPR minima that are approximately 800 cm$^{-1}$ apart. Comparison of the theoretical SPR spectrum 304 with spectra 302 and 306 obtained by the two approach directions shows that a certain amount of error is present in both, with the high-to-low direction matching the theoretical output more closely (+270 cm$^{-1}$ versus −570 cm$^{-1}$ error). However, approaching from lower incident angles yielded marginally better reproducibility.

The two most accessible user-definable parameters in SPR analysis are the incident angle and the wavelength of light. In a typical experiment, one of these parameters is held constant while shifts in the other are correlated to changes in near-surface refractive index. If neither of these parameters are fixed, surface plasmons will be coupled at multiple angles and at multiple wavelengths simultaneously. This, in turn, will lead to broad SPR dips with nearly imperceptible minima. Accordingly, a slit width of aperture 210 may effect the SPR dip.

Figure 4:
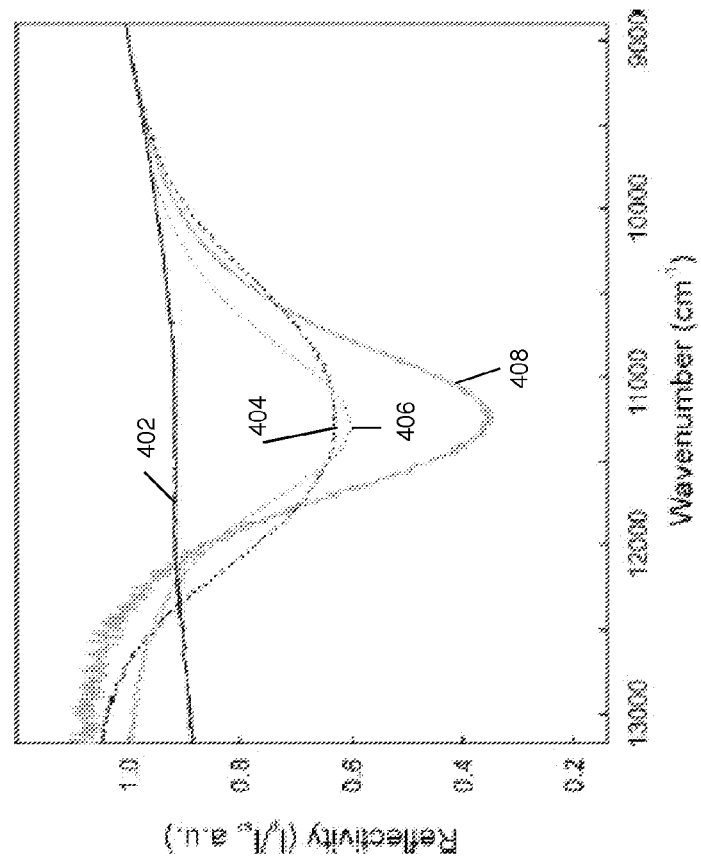
FIG. 4 is a graph of reflectivity as a function of wavenumber illustrating example SPR spectra for various approaching aperture sizes, according to an embodiment of the present invention.

Referring to FIG. 4, a graph of reflectivity as a function of wavenumber illustrating example SPR spectra for various approaching aperture sizes is shown. In particular, curve 402 represents no aperture 210 (FIG. 2A) (i.e., no plate 208); curve 404 represents a 3 mm wide aperture; curve 406 represents a 1 mm wide aperture; and curve 408 represents a 0.2 mm wide aperture. In an exemplary SPR accessory 104 (FIG. 2A), polarized beam 212 is focused onto the planar surface of hemispherical prism 222 with a beam spread of approximately ±10°. Without aperture 210 (FIG. 2A), curve 402 shows no SPR dip was observed.

The angular spread may be limited by introducing aperture 210 (FIG. 2A) (effectively an f-stop) to limit the spread of incident angles, inducing SPR accessory 104 to perform similarly to a conventional multi-wavelength configuration but with collimated light, and yielding the classical SPR dip (curves 404-408). The beam spread decreases to ±1.2°, ±0.8°, and ±0.7° by adding respective apertures of 3-mm, 1-mm, and 0.2-mm widths.

The quality of SPR dips may also be determined directly from the spectra by calculating the ratio of the full width at half maximum (FWHM) and the intensity drop. With this approach, lower numbers indicate more desirable dips (i.e., narrower FWHM with a higher intensity drop). For the SPR dips collected with the aforementioned apertures, the FHWM/intensity ratio decreases from 60, to 32, to 20.

Both ray-tracing and FWHM analysis indicate that in order to obtain substantially sharper dips, it may be desirable to include apertures significantly smaller than 0.2 mm. However, restricting the angular spread further also decreases the photon throughput, leading to poorer signal-to-noise ratios (SNR). In order to compensate for lower SNRs, narrower apertures require greater spectral averaging with subsequently longer analysis times and a loss in temporal resolution. At the other extreme, wide apertures yield improved SNR, but the increased angular spread will result in shallower dips, meaning that locating the dip minima may become challenging. Hence, the choice in aperture may be tailored to the intended application. Because the results presented here involve exclusively static measurements, a 1-mm-wide aperture was used, as it presented what was considered a good compromise between dip sharpness and analysis time (85 s for 100 scans averaged at 4 cm$^{-1}$).

Figure 5:
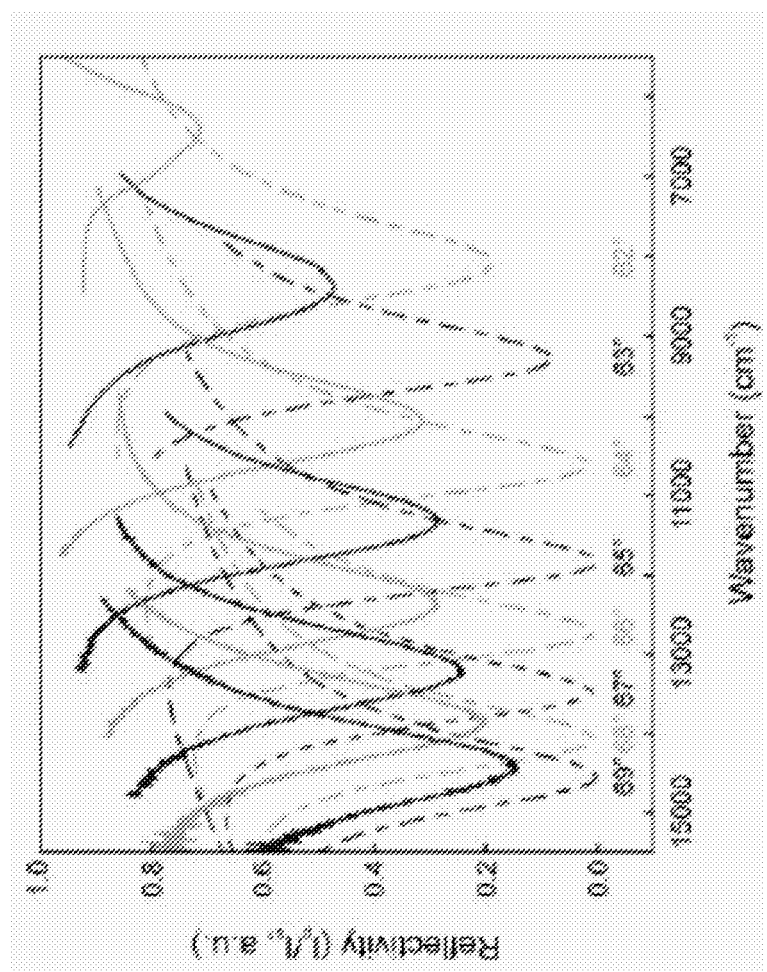
FIG. 5 is a graph of reflectivity as a function of wavenumber illustrating example measured and theoretical SPR spectra for various incident angles, according to an embodiment of the present invention.

Wavelength tunability of the modified accessory was verified by step-wise adjustment of the angle of incidence. Referring to FIG. 5, a graph of reflectivity as a function of wavenumber illustrating example measured and theoretical SPR spectra for various incident angles is shown. FIG. 5 graphically summarizes the change in SPR minima obtained in deionized water between 62° and 69°. The location of the SPR dip may be tuned by appropriately selecting the incident angle. The ability to tune the SPR dip location is of special interest in applications such as plasmon-enhanced absorption spectroscopy, where the SPR dip is overlaid onto absorption features from the analyte. Fresnel modeling of the SPR response to deionized water at 20° C. is superimposed onto the experimental counterparts and presented in FIG. 5.

Figure 6A:
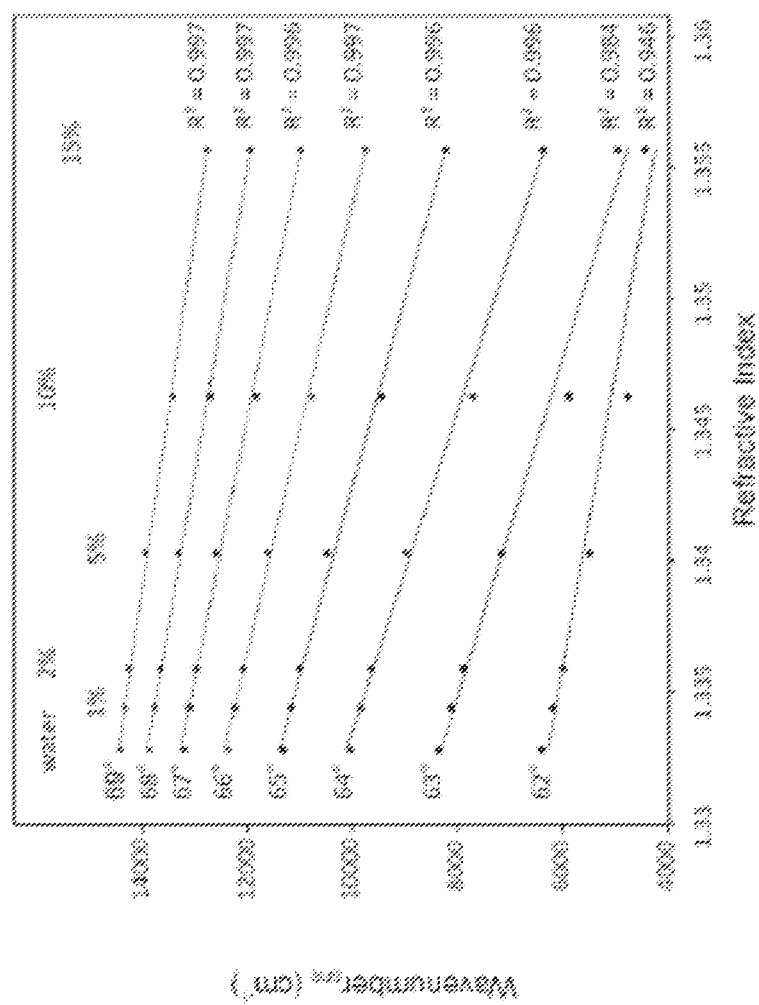
FIG. 6A is a graph of wavenumber as a function of refractive index illustrating example calibration curves for samples with different sucrose concentrations, according to an embodiment of the present invention.

Another figure of merit is the sensitivity of the SPR method proposed as a function of refractive index. Referring to FIG. 6A, a graph of wavenumber as a function of refractive index illustrating example calibration curves for samples with different sucrose concentrations is shown. The calibration curves were obtained at the incident angles compatible with aqueous measurements. The sensitivities obtained are also summarized in Table 2.

TABLE 2

Comparison of location of dip minima
and sensitivity per angle tested

| Incident angle (°) | Experimental wavenumber (cm$^{-1}$) | Theoretical wavenumber (cm$^{-1}$) | Sensitivity (×10$^3$ cm$^{-1}$/RIU) |
|---|---|---|---|
| 62 | 6409 ± 14 | 8084 | −86 ± 0.6 |
| 63 | 8354 ± 25 | 9268 | −150 ± 1.1 |
| 64 | 10055 ± 34 | 10620 | −160 ± 1.5 |
| 65 | 11318 ± 25 | 11830 | −135 ± 1.0 |
| 66 | 12378 ± 25 | 12720 | −114 ± 0.7 |
| 67 | 13214 ± 25 | 13480 | −98 ± 0.7 |
| 68 | 13871 ± 30 | 14060 | −84 ± 1.2 |
| 69 | 14434 ± 20 | 14530 | −73 ± 0.6 |

The response of the SPR accessory 104 (FIG. 2A) to changes in sample RI increases in sensitivity with decreasing incident angle or increasing probing wavelength. The increase in sensitivity with respect to wavelength is tied to the dielectric constant of the gold thin film. Succinctly, this means that for a fixed angle, the measured wavenumber for a given change in refractive index may be greater at longer wavelengths. A downside to utilizing longer excitation wavelengths with planar metal films is that plasmonic propagation lengths increase concomitantly (approximately 11 μm and 135 μm for 14434 cm$^{-1}$ (69° and 6409 cm$^{-1}$ (62° for gold, respectively); therefore, long wavelengths may be less attractive to imaging applications due to the loss in spatial resolution. Another effect accompanying longer excitation wavelengths involves the penetration depth of the plasmonic wave into the sample. At 14434 cm$^{-1}$ (69°, the plasmonic wave extends approximately 270 nm into the aqueous medium, versus approximately 1630 nm for excitation at 6409 cm$^{-1}$ (62°. The increase in probed analytical volume results in a SPR response that is less sensitive to changes in near-surface RI and resembles more closely bulk RI changes.

The reproducibility of the response to different RIs and the angle repeatability of SPR accessory 104 is illustrated in FIG. 6A. As outlined above, each data point was obtained by changing both solutions and angles simultaneously. Still, the resulting error bars (±1σ) in FIG. 6A are small. The standard deviation for each data point ranged from ±4 cm$^{-1}$ to ±36 cm$^{-1}$.

Figure 6B:
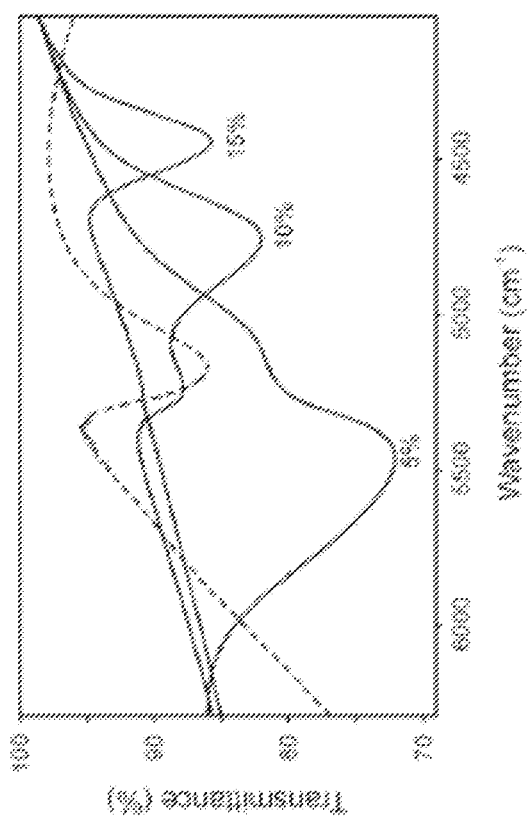
FIG. 6B is a graph of transmittance as a function of wavenumber illustrating SPR dips for several different sucrose concentrations, according to an embodiment of the present invention.

In FIG. 6A, a deviation from linearity is observed for the data acquired at incident angles of 62° and 63°. Part of the problem with determining the wavenumber with dips around 5000 cm$^{-1}$ involves interference from the absorption features of water. Referring to FIG. 6B, a graph of transmittance as a function of wavenumber is shown, which illustrates SPR dips for several different sucrose concentrations. In particular, FIG. 6B illustrates the SPR dips obtained at 62° for the three highest sucrose concentrations (solid lines) and a conventional reflection spectrum of water (dashed line) illustrating the influence of absorption features on SPR spectra. In both cases the SPR dips are not fully resolved due to a negative plasmon enhancement. Therefore, accurate determination of the wavenumber may not possible at this angle, due to a lack of RI values for sucrose solutions at those wavenumbers.

Figure 7A:
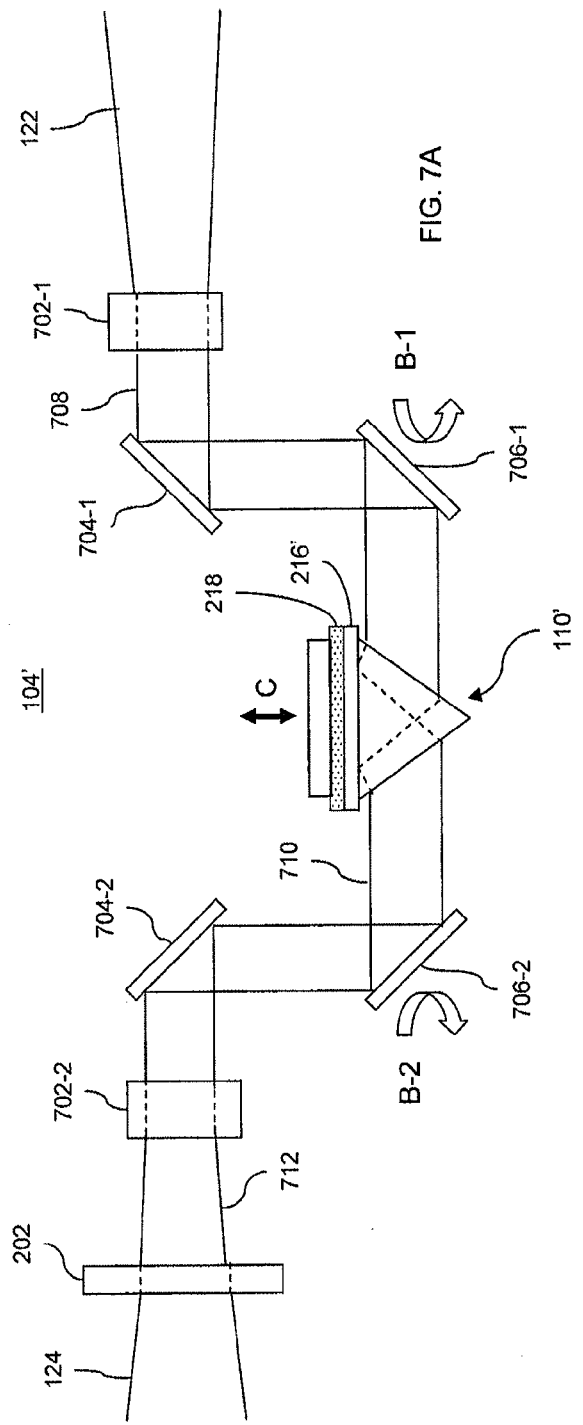
FIG. 7A is a schematic diagram of an exemplary SPR accessory used in the spectrometer shown in FIG. 1, according to another embodiment of the present invention.
Figure 7B:
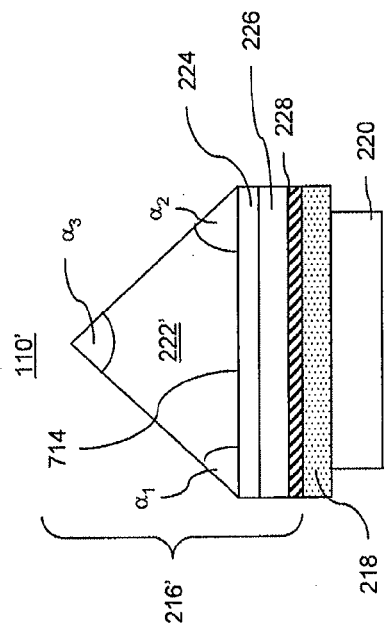
FIG. 7B is a cross-sectional diagram of an exemplary sample cell of the SPR accessory shown in FIG. 7A, according to an embodiment of the present invention.

Referring next to FIGS. 7A and 7B, SPR accessory 104' is described, according to another embodiment of the present invention. In particular, FIG. 7A is a schematic diagram SPR accessory 104'; and FIG. 7B is a cross-sectional diagram of sample cell 110'.

Referring to FIG. 7A, SPR accessory 104 includes negative lenses 702-1, 702-2, fixed planar mirrors 704-1, 704-2, tiltable mirrors 706-1, 706-2, sample cell 110' and polarizer 202. Fixed mirrors 704-1, 704-2 and tiltable mirrors 706-1, 706-2 represent mirror system 112 (FIG. 1). Tiltable mirrors 706-1, 706-2 are configured to be rotatably positioned, as indicated by respective arrows B-1, B-2, for example by mirror drive 118 (FIG. 1). Polarizer 202 and negative lenses 702-1, 702- represent SPR conversion optics 114 (FIG. 1). Sample cell 110' may be translated relative to mirrors 704-1, 704-2 as indicated by double arrow C, for example, by sample cell drive 116 (FIG. 1). SPR accessory 104' is similar to SPR accessory 104 (FIG. 2A), except that SPR accessory 104' includes negative lenses 702 and fixed planar mirrors 704, instead of plane 208 having aperture 210 and fixed elliptical mirrors 206.

As shown in FIG. 7B, sample cell 110' is similar to sample cell 110 (FIG. 2B), except that sample cell 110' includes SPR structure 216' having triangular prism 222', instead of hemispherical prism 222. Triangular prism 222' includes active surface 714 for reflecting light beam 708. Triangular prism includes interior angles $\alpha_1$, $\alpha_2$ and $\alpha_2$, with interior angle $\alpha_3$ being opposite active surface 714. Although triangular prism 222' is illustrated, it is understood that prism 222' is not limited to a triangular prism, and may including hemispherical prism 222 (FIG. 2B) as well as any polygonal shaped prism (such as shown in FIGS. 11B and 11C). Although FIG. 7A illustrates sample cell 110' configured with sample 218 above prism 222', sample cell 110' may also be configured with prism 222' above sample 218, for example, as shown in FIGS. 9A and 9B.

Referring back to FIG. 7A, in operation, negative lens 702-1 is configured to receive broadband light beam 122 and to collimate light beam 122, forming collimated beam 708. Collimated beam 708 is directed by fixed mirror 704-1 and tiltable mirror 706-1 onto sample cell 110'. Tiltable mirrors 706-1, 706-2 may be simultaneously adjusted to direct collimated beam 708 to sample cell 110' at different incident angles.

Collimated beam 708 is directed through prism 222' and onto film 228. Collimated beam 708 undergoes internal reflection in prism 222 and is reflected off of film 228 and out of sample cell 110'. SPR modified beam 710 output from prism 222' is modified by the SPR produced between SPR structure 216' and sample 218. The spatial location of sample cell 110' may also be adjusted in concert with the rotation of tiltable mirrors 706-1, 706-2, to maintain reflectance off of a center of active surface 714 of prism 222' and reflection of SPR modified beam 710 towards tiltable mirror 706-2.

SPR modified beam 710 output from prism 222' may be directed to negative lens 702-2 via tiltable mirror 706-2 and fixed mirror 704-2. Negative lens 702-2 may diverge SPR modified beam 710 to match collection optics (not shown) of spectrometer 100 (FIG. 1), forming diverged beam 712. Polarizer 202 may select between parallel (reference) and perpendicular (analytic signal) polarized light, to form output beam 124.

Although FIG. 7A illustrates polarizer 202, a similar result may be achieved, as discussed above, by collecting a reference SPR spectrum of sample 218 in air (refractive index of about 1.0) and a further SPR spectrum of sample 218 in water (refractive index of about 1.33) and comparing the two SPR spectrum.

The geometry of prism 222', specifically interior angles $\alpha_1$, $\alpha_2$ and $\alpha_3$ (FIG. 7B), may be selected to control the angle of light directed to active surface 714. Referring to FIGS. 8A-8C, cross-sectional diagrams are shown of prisms 222' having different interior angles. For example, In FIG. 8A, prism 222' has respective interior angles $\alpha_1$, $\alpha_2$ and $\alpha_3$ of 45°, 45° and 90°. In FIG. 8B, prism 222' has respective interior angles $\alpha_1$, $\alpha_2$ and $\alpha_3$ of 60°, 60° and 60°. In FIG. 8C, prism 222' has respective interior angles $\alpha_1$, $\alpha_2$ and $\alpha_3$ of 75°, 75° and 30°.

FIGS. 8A-8C illustrate that different example dimensions of the prism 222' may be selected depending upon the desired incident angle of light beam 802 on active surface 714. A 'sharper' prism (for example, FIG. 8C with respective interior angles $\alpha_1$, $\alpha_2$ and $\alpha_3$ of 75°, 75° and 30°), may allow access to more shallow angles and hence a higher refractive index (for example, organic solvents), and analysis further in the IR range for lower RI samples (for example, aqueous at 15 µM). Broader prisms (for example, FIG. 8A with respective interior angles $\alpha_1$, $\alpha_2$ and $\alpha_3$ of 45°, 45° and 90°), may allow better accessibility to steeper angles and thus may be used for lower RI samples (for example, gasses).

Referring next to FIGS. 9A and 9B, SPR accessory 104' is shown, illustrating control of the angle of incidence via positioning of tiltable mirrors 706-1 and translation of prism 222'. In FIGS. 9A and 9B, prism 222' represents a ZnSe prism respective interior angles $\alpha_1$, $\alpha_2$ and $\alpha_3$ of 45°, 45° and 90°. A traveling length of ZnSe prism 222' (in a vertical direction illustrated by double arrow C in FIG. 7A) is about 125 mm. A diameter of collimated beam 708 is about 6.4 mm.

In FIG. 9A, tiltable mirror 706-1 is positioned at a 15° angle relative to the horizontal. Prism 222' is positioned such that collimated beam 708 has an AOI of 39°. In FIG. 9B, tiltable mirror 706-1 is positioned at a 7° angle relative to the horizontal. Prism 222' is positioned such that collimated beam 708 has an AOI of 33°.

The generalized optical train, illustrated in FIGS. 9A and 9B as an example with a ZnSe prism, may be applied to multiple different prism materials and sample RIs. The angle of incidence (AOI) at the prism/sample interface used to excite a surface plasmon is a function of the refractive index of prism 222' and the refractive index of sample 218. For a prism of a particular material and dimension, the AOI may be systematically varied by rotating tiltable mirrors 706-1, 706-2.

For ease in collection of the reflected light 710 to determine the surface plasmon reflected spectra, rotating mirrors 706 in concert with appropriately translating (i.e., raising or lowering) prism 222' may insure that light beam 708 reflects off of the center of prism 222'. Accordingly, the same spot may be interrogated with all incident angles. Each prism 222' may have an inherent travel length of vertical translation that will correspond to the range of incident angles that may be accessed while maintaining a single reflection off the center of prism 222'.

Figure 10A:
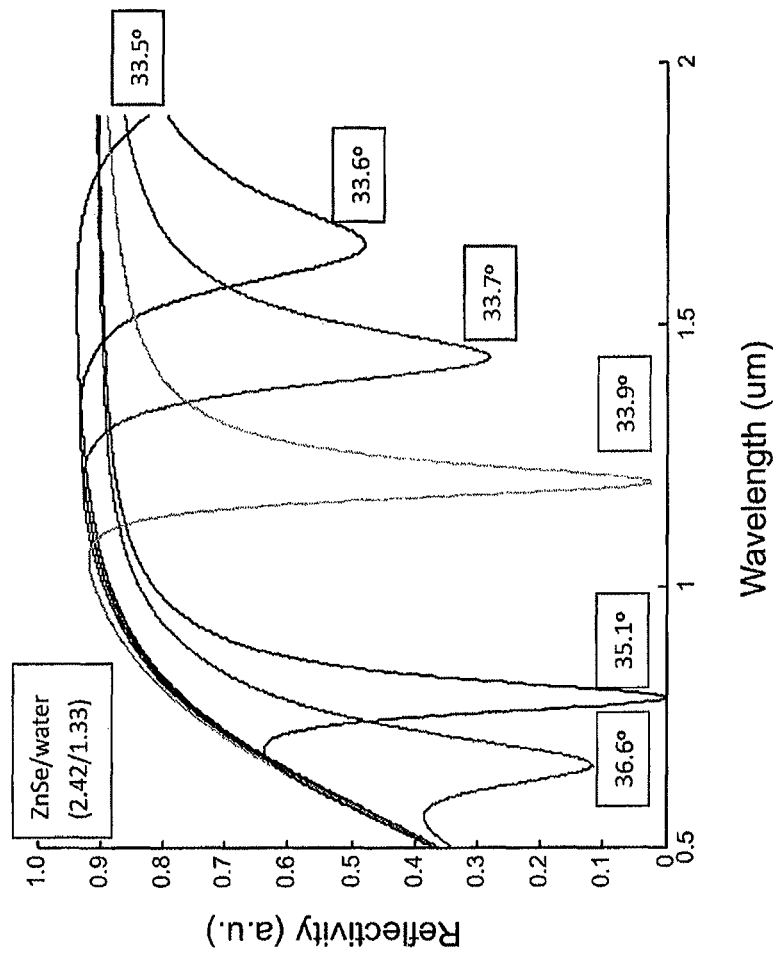
FIGS. 10A, 10B and 10C are graphs of reflectivity as a function of wavelength illustrating example SPR spectra simulated using the SPR accessory shown in FIG. 7A for various incident angles, according to an embodiment of the present invention.
Figure 10B:
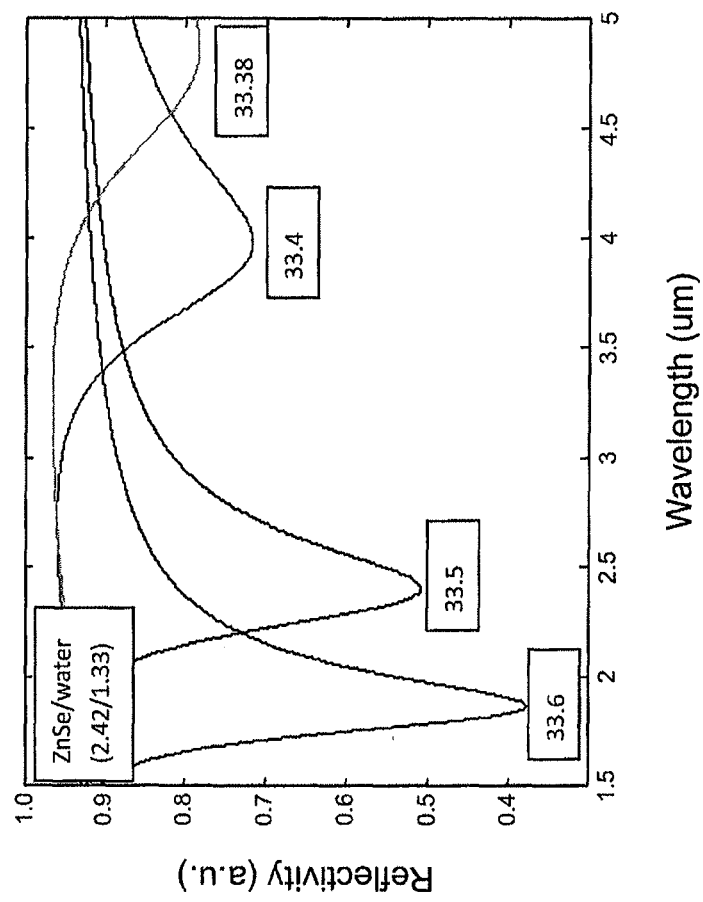
Figure 10C:
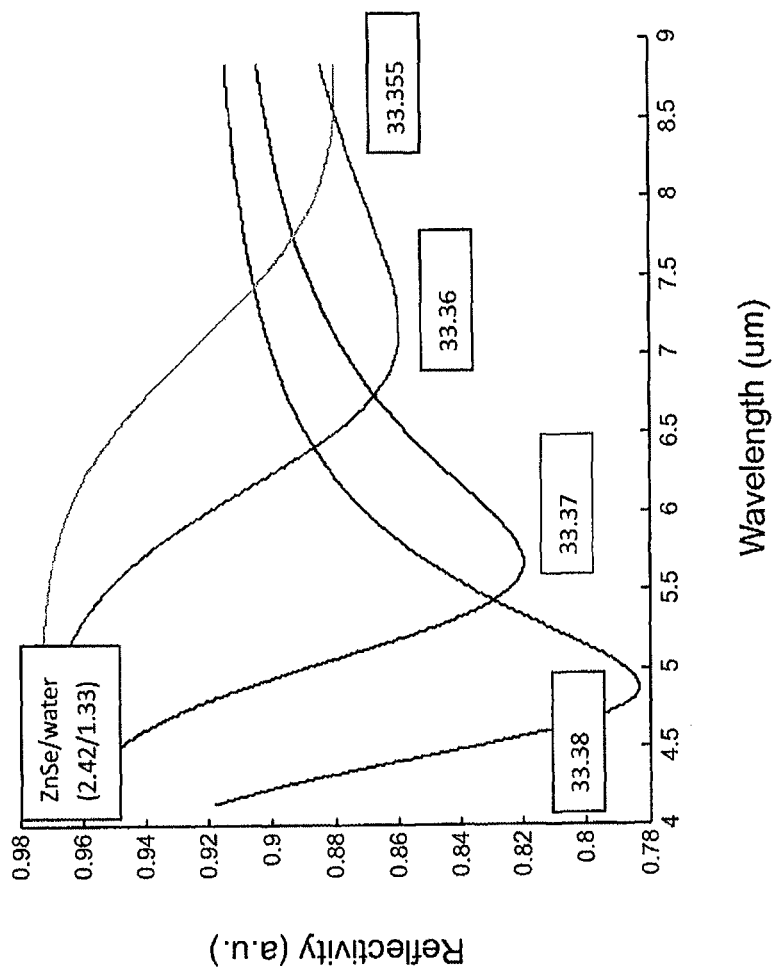

Referring to FIGS. 10A-10C, graphs of reflectivity as a function of wavelength are shown illustrating example SPR spectra. The example SPR spectra are predicted from the Fresnel equations using SPR accessory 104' (FIG. 7A) for a prism 222' of ZnSe (refractive index of 2.42) in an aqueous solution (refractive index of 1.33) for various incident angles. FIGS. 10A-10C show that ZnSe displays appropriate optical and physical properties that may ZnSe a suitable material for SPR spectroscopy over a wide range of wavelengths.

Although FIGS. 2A and 7A illustrate prisms 222 and 222' of respective hemispherical and triangular shapes, in general, the shape of prism 222 (in FIG. 2A) and prism 222' (in FIG. 7A) may be of any suitable geometry to allow access to a suitable range of angles of incidence (AOI) for SPR spectroscopy.

Referring to FIGS. 11A, 11B and 11C, different example geometries of respective prisms 222', 222" and 222'" are shown, illustrating respective AOIs achieved by these geometries. In particular, FIG. 11A is a cross-section diagram of triangular prism 222'; FIG. 11B is a cross-section diagram of trapezoidal prism 222"; and FIG. 11C is a cross-section diagram of pentagonal prism 222'".

Referring to FIG. 11A, prism 222' is a triangular-shaped prism (a right triangle) formed of ZnSe, where ZnSe has refractive index of about 2.42. For ZnSe, a right-angled triangle geometry allows access to a range of AOIs suitable for SPR spectroscopy.

Incident light beam 1104 is refracted into prism 222', to form refracted beam 1106. Refracted beam 1106 is reflected from active surface 1102 to form reflected beam 1108. If refracted beam 1106 is reflected from active surface 1102 at an angle (i.e., an AOI) of 36.6°, the SPR dip is expected to display a reflectivity minimum at about 0.7 µm for a sample with a refractive index of 1.33 (such as water). Reflected beam 1108 is refracted out by prism 222', to form output beam 1110. By launching incident light beam 1104 at steeper angles (such that refracted beam 1106 is at a steeper angle with respect to active surface 1102), the SPR dip can be tuned to resonate (display a minimum) at longer wavelengths. For example, at 33.355°, the SPR dip is expected to resonate at about 8.5 µm.

Referring to FIG. 11B, prism 222" is a trapezoidal-shaped prism (sometimes referred to as a "dove prism") formed of $CaF_2$, where $CaF_2$ has a refractive index of about 1.43. For $CaF_2$, a prism geometry such as a trapezoid may allow access to a range of AOIs suitable for SPR spectroscopy. For this example trapezoidal geometry, the SPR dip may be tuned, for example, between about 0.74 µm to about 8.6 µm with respective AOIs between about 78° to about 68.51°.

Referring to FIG. 11C, prism 222'" is a pentagonal-shaped prism (sometimes referred to as a "penta prism") formed of Ge, where Ge has a refractive index of about 4.02. For Ge, a prism geometry such as a pentagon may allow access to a range of AOIs suitable for SPR spectroscopy. For this example geometry, an AOI of 19.5° at active surface 1102 may result in a dip at about 1.6 µm. As another example, an AOI of 19.33° would shift the SPR dip to about 8 µm. Similar to Ge, a Si (refractive index of about 3.42) penta prism 220'" may also accommodate SPR spectroscopy. For Si, the AOI range may include between about 23.3° to about 22.9°, for respective SPR dips at about 1 µm to about 7 µm.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An accessory for an infrared (IR) spectrometer, the accessory comprising:
   an input port and an output port having an optical path therebetween;
   a surface plasmon resonance (SPR) structure for contacting a sample, the SPR structure configured to produce internally reflected light responsive to broadband IR light, the internally reflected light modified by a surface plasmon resonance produced between the SPR structure and the sample;
   a mirror system configured to direct the broadband IR light from the input port to the SPR structure and to direct the internally reflected light from the SPR structure to the output port to produce output light indicative of a characteristic of the sample associated with the surface plasmon resonance; and an optical element disposed along the optical path between the input port and the output port, configured to produce collimated light, wherein the mirror system includes at least one elliptical mirror.

2. The accessory according to claim 1, wherein the optical element includes a plane having an aperture configured to produce the collimated light.

3. The accessory according to claim 2, wherein the aperture includes a slit and a width of the slit is between about 0.1 mm to about 4 mm.

4. The accessory according to claim 1, further including a polarizer disposed along the optical path between the input port and the output port, the polarizer configured to produce polarized light.

5. The accessory according to claim 1, wherein the accessory is configured to be integrated into a sample chamber of the IR spectrometer.

6. The accessory according to claim 1, further including a drive coupled to the SPR structure, the drive configured to translate the SPR structure relative to the mirror system.

7. The accessory according to claim 1, further including a drive coupled to the mirror system, the drive configured to rotate at least one mirror of the mirror system.

8. The accessory according to claim 1, wherein the SPR structure includes:
   a prism having a surface for receiving the broadband IR light and an active surface adjacent to the sample for internally reflecting the broadband IR light; and
   a film disposed between and in contact with the active surface of the prism and the sample, the film configured to produce the surface plasmon resonance at an interface between the film and the sample.

9. The accessory according to claim 8, wherein a shape of the prism includes at least one of: a hemisphere, or a polygon having at least three sides.

10. The accessory according to claim 8, wherein a material of the prism includes at least one of: glass, sapphire, BK-7, germanium (Ge), zinc sulfide (ZnS), zinc selenide (ZnSe), silicon (Si), thallium halogenide, calcium fluoride ($CaF_2$), barium fluoride (BaF2), potassium bromide (KBr), sodium chloride (NaCl) or magnesium fluoride ($MgF_2$).

11. The accessory according to claim 8, wherein a material of the film includes at least one of gold, silver, aluminum, indium tin oxide (ITO) or metallic nanoparticles.

12. An accessory for an infrared (IR) spectrometer, the accessory comprising:
   an input port and an output port having an optical path therebetween;
   a surface plasmon resonance (SPR) structure for contacting a sample, the SPR structure configured to produce internally reflected light responsive to broadband IR light, the internally reflected light modified by a surface plasmon resonance produced between the SPR structure and the sample;
   a mirror system configured to direct the broadband IR light from the input port to the SPR structure and to direct the internally reflected light from the SPR structure to the output port to produce output light indicative of a characteristic of the sample associated with the surface plasmon resonance; and
   an optical element disposed along the optical path between the input port and the output port, configured to produce collimated light,
   wherein the optical element configured to produce the collimated light includes a negative lens positioned between the input port and the SPR structure, the negative lens configured to direct the collimated light to the SPR structure.

13. The accessory according to claim 12, wherein the accessory includes a further negative lens positioned between the SPR structure and the output port, the further negative lens configured to decollimate the internally reflected light from the SPR structure.

14. An accessory for an infrared (IR) spectrometer, the accessory comprising:
   an input port and an output port having an optical path therebetween;
   a surface plasmon resonance (SPR) structure for contacting a sample, the SPR structure configured to produce internally reflected light responsive to broadband IR light, the internally reflected light modified by a surface plasmon resonance produced between the SPR structure and the sample;
   a mirror system configured to direct the broadband IR light from the input port to the SPR structure and to direct the internally reflected light from the SPR structure to the output port to produce output light indicative of a characteristic of the sample associated with the surface plasmon resonance; and
   an optical element disposed along the optical path between the input port and the output port, configured to produce collimated light,
   wherein the SPR structure includes:
      a prism having a surface for receiving the broadband IR light and an active surface adjacent to the sample for internally reflecting the broadband IR light; and
      a film disposed between and in contact with the active surface of the prism and the sample, the film configured to produce the surface plasmon resonance at an interface between the film and the sample, and
   wherein the film is disposed on a coverslip and the SPR structure includes a refractive index matching fluid between the prism and the coverslip.

15. A method of measuring a characteristic of a sample, the method comprising the steps of:
   directing broadband infrared (IR) light via a mirror system to a surface plasmon resonance (SPR) structure for contacting the sample,
   internally reflecting the broadband IR light at an interface between the SPR structure and the sample, producing at the interface a surface plasmon resonance that modifies the internally reflected light;
   directing the internally reflected light from the SPR structure via the mirror system to produce output light indicative of the surface plasmon resonance; and
   measuring the output light to determine the characteristic of the sample,
   wherein the characteristic is associated with the surface plasmon resonance, and the broadband IR light or the output light is collimated, and
   wherein the mirror s stem includes at least one elliptical mirror.

16. The method according to claim 15, wherein the method includes the step of passing the broadband IR light through an aperture of a plane to produce collimated light or the step of passing the output light through an aperture of a plane to produce collimated light.

17. The method according to claim 15, wherein the measuring of the output light includes measuring a spectrum of the output light, the spectrum indicating the characteristic of the sample.

18. The method according to claim 15, wherein the method further includes translating the SPR structure relative to the mirror system to control an angle of incidence of the broadband IR light at the interface between the SPR structure and the sample.

19. The method according to claim 15, wherein the method further including rotating at least one mirror of the mirror system to control an angle of incidence of the broadband IR light at the interface between the SPR structure and the sample.

20. The method according to claim 15, wherein the SPR structure includes a prism and a film disposed between the prism and the sample, and the internally reflecting of the broadband IR light includes:
    passing the broadband IR light from a surface of the prism to an active surface of the prism adjacent to the sample;
    producing the surface plasmon resonance between the film and the sample responsive to the broadband IR light at the active surface of the prism; and
    reflecting the broadband IR light modified by the surface plasmon resonance from the active surface out of the prism, to produce the internally reflected light.

21. The method according to claim 20, wherein a shape of the prism is selected to produce a predetermined angle of incidence of the broadband IR light at the interface between the SPR structure and the sample.

22. The method according to claim 15, wherein the broadband IR light or the output light is polarized.

23. A method of measuring a characteristic of a sample, the method comprising the steps of:
    directing broadband infrared (IR) light via a mirror system to a surface plasmon resonance (SPR) structure for contacting the sample,
    passing the broadband IR light through a negative lens to produce collimated light;
    directing the collimated light to the SPR structure;
    internally reflecting the broadband IR light at an interface between the SPR structure and the sample, producing at the interface a surface plasmon resonance that modifies the internally reflected light;
    directing the internally reflected light from the SPR structure via the mirror system to produce output light indicative of the surface plasmon resonance; and
    measuring the output light to determine the characteristic of the sample,
    wherein the characteristic is associated with the surface plasmon resonance, and the broadband IR light or the output light is collimated.

24. The method according to claim 23, wherein the method further includes:
    passing the internally reflected light from the SPR structure through a further negative lens to produce decollimated light, the decollimated light being directed by the mirror system to produce the output light.

* * * * *